(12) United States Patent
Huang et al.

(10) Patent No.: US 9,087,141 B2
(45) Date of Patent: Jul. 21, 2015

(54) ANALYSIS MODULE, CLOUD ANALYSIS SYSTEM AND METHOD THEREOF

(71) Applicant: National Central University, Jhongli, Taoyuan County (TW)

(72) Inventors: Norden Eh Huang, Jhongli (TW); Men-Tzung Lo, Jhongli (TW); Bo-Jau Kuo, Taipei (TW); Yu-Cheng Lin, Taipei (TW)

(73) Assignee: NATIONAL CENTRAL UNIVERSITY, Jhongli, Taoyuan County (TW)

(*) Notice: Subject to any disclaimer, the term of this patent is extended or adjusted under 35 U.S.C. 154(b) by 180 days.

(21) Appl. No.: 13/714,260

(22) Filed: Dec. 13, 2012

(65) Prior Publication Data
US 2014/0067838 A1    Mar. 6, 2014

(30) Foreign Application Priority Data
Aug. 29, 2012  (TW) .............................. 101131315 A

(51) Int. Cl.
G06F 17/30    (2006.01)
G06F 19/00    (2011.01)

(52) U.S. Cl.
CPC .......... *G06F 17/30943* (2013.01); *G06F 19/30* (2013.01)

(58) Field of Classification Search
CPC .............. G06F 17/14; G06F 17/30943; G06F 17/30091; G06F 17/30386; A61K 2300/00; A61K 45/06
USPC .......................................... 707/758, 822, 825
See application file for complete search history.

(56) References Cited

U.S. PATENT DOCUMENTS

| | | | |
|---|---|---|---|
| 2003/0033094 A1* | 2/2003 | Huang ............................ | 702/39 |
| 2004/0138558 A1* | 7/2004 | Dunki-Jacobs et al. ...... | 600/431 |
| 2006/0220037 A1* | 10/2006 | Hanamaki et al. .............. | 257/82 |

OTHER PUBLICATIONS

Zou et al., Speech enhancement based on Hilbert-Huang transform theory, 2006, IEEE, 6 pages.*
Chin-Feng Lin et al., A HHT-based Time Frequency Analysis Scheme in Clinical Alcoholic EEG Signals, Oct. 2008, Issue 10, vol. 5, 249-260.*

* cited by examiner

*Primary Examiner* — Jean B Fleurantin
(74) *Attorney, Agent, or Firm* — Muncy, Geissler, Olds & Lowe, P.C.

(57) ABSTRACT

An analysis module is provided in the invention. The analysis module is connected with a database containing several data. The analysis module comprises an analysis unit and a database managing system. The analysis unit is developed by a development software to combine HHT algorithm and an automatic data-loading program. The database managing system is integrated in the analysis unit and connected with the database. The data are transferred to the analysis unit by the database managing system, and the analysis unit is used to load the data by the automatic data-loading program and analyzes the data.

17 Claims, 8 Drawing Sheets

2012/07/12- systolic pressure information during the week

2012/07- systolic pressure information during the month

All systolic pressure information before 2012/07/12

ANALYSIS MODULE, CLOUD ANALYSIS SYSTEM AND METHOD THEREOF

CROSS-REFERENCE TO RELATED APPLICATIONS

This Non-provisional application claims priority under 35 U.S.C. §119(a) on Patent Application No(s). 101131315 filed in Taiwan, Republic of China Aug. 29, 2012, the entire contents of which are hereby incorporated by reference.

FIELD OF THE INVENTION

The invention relates to an analysis module and, more particularly, to an automatic cloud analysis system.

BACKGROUND OF THE INVENTION

As improved development of technology, more and more sensing devices are used to detect physiology signals. These sensing devices can provide users to detect health condition by themselves. However, the physiology signals are variation and complex. These physiology signals are not systematically arranged well. The user always obtains only the current health information, not the personal physiological parameters long-term change of trend.

In view of the prior art of No. I286714 of TW patent, I286714 discloses a portable tele-homecare physiological signal monitoring system to monitor the change of physiological signals in the user's home life. The portable tele-homecare physiological signal monitoring system includes at least one data-distributed server, at least one sensing device, and at least one first user computer. The sensing device and the first user computer are connected to the data-distributed server.

When the user's physiological signal is abnormal, the data-distributed server sends a warning message to the preset mobile phone, PDA or a preset e-mail address to immediately notify the user's family or physicians. Such health management system only can provide simple diagnosis of physiology signal to inform the user the current physiological condition, but not for the long-term change of trend.

Other off-line analysis health management system is complex, and not only requires large resources, but also requires professionals to operate and analyze. The infrastructure of the off-line analysis health management system costs high and the analysis results still needs to spend more manpower and time.

SUMMARY OF THE INVENTION

An analysis module is provided in the invention. The analysis module is connected with a database, and the database contains several data. The analysis module comprises an analysis unit and a database managing system.

The analysis unit is developed by a development software to combine Hilbert Huang Transform (HHT) algorithm and an automatic data-loading program. The database managing system is integrated in the analysis unit and connected with the database.

After the data are transferred to the analysis unit by the database managing system, the analysis unit is used to load the data by the automatic data-loading program and analyze the data. The data can be physiology parameter data, but not limited herein. The data contain various linear data, non-linear data, stationary data and non-stationary data, but not limited herein.

The database of the invention can constantly store all kinds of data. The analysis module can execute searching and reading through the database managing system and the database. The data are transferred to the analysis unit by the database managing system, and the analysis unit is used to load the data by the automatic data-loading program and analyzes the data to generate an analysis result.

The invention also provides a cloud analysis system. The cloud analysis system comprises a server end and a user end. The server end of the invention comprises a database, an analysis module and an output unit.

The characteristics of the analysis module of the cloud analysis system in the invention are descriptor above. The output unit comprises an output interface.

The user end of the cloud analysis system is connected to the sever end, and the user end comprises at least a sensing device. The data of the database are the results from the sensing device.

The data are transferred to the analysis unit by the database managing system, and the analysis unit is used to load the data by the automatic data-loading program and analyzes the data to generate an analysis result. The analysis result can be displayed to the general web browser for the user's query or instantly transferred to the user by the output interface, but not limited herein.

A cloud analysis method is also provided in the invention. The cloud analysis method is applied to a server end, and the sever end comprises a database containing several data. The data of the database are the results from at least a sensing device. The cloud analysis method comprises the steps as follows:

Step. 1 The data are transferred to an analysis unit by a database managing system.

Step. 2 The analysis unit is used to load the data by an automatic data-loading program and analyzes the data. Wherein, the analysis unit is developed by a development software to combine HHT algorithm and an automatic data-loading program.

Step. 3 Results from the analysis unit are outputted by an output interface.

In fact, the cloud analysis system of the invention is a fully automated cloud health management system. The sensing device, such as health measurement device, can upload physiology parameter data to the sever end by wire or wireless way. The data can be automatically recorded, stored and analyzed on network cloud to provide users fully automatic and comprehensive analysis service. The cloud analysis system uses the empirical mode decomposition of HHT to decompose the any complex raw data into a number of intrinsic mode functions and a non-oscillatory trend and further to provide referable information. The intrinsic mode function can be used as personal physiological parameters information of fluctuation in the days, weeks, or months. The non-oscillatory trend has been ruled out transient noise or instantaneous fluctuations. As a result, the non-oscillatory trend can be taken as the personal physiological parameters trend. The user is allowed to easily obtain his physical condition and information through the cloud network.

These and other features, aspects and advantages of the disclosure will become better understood with regard to the following description, appended claims, and accompanying drawings.

DETAILED DESCRIPTION OF THE INVENTION

For clarity of disclosure, and not by way of limitation, the detailed description of the invention is divided into the subsections that follow.

Figure 1:
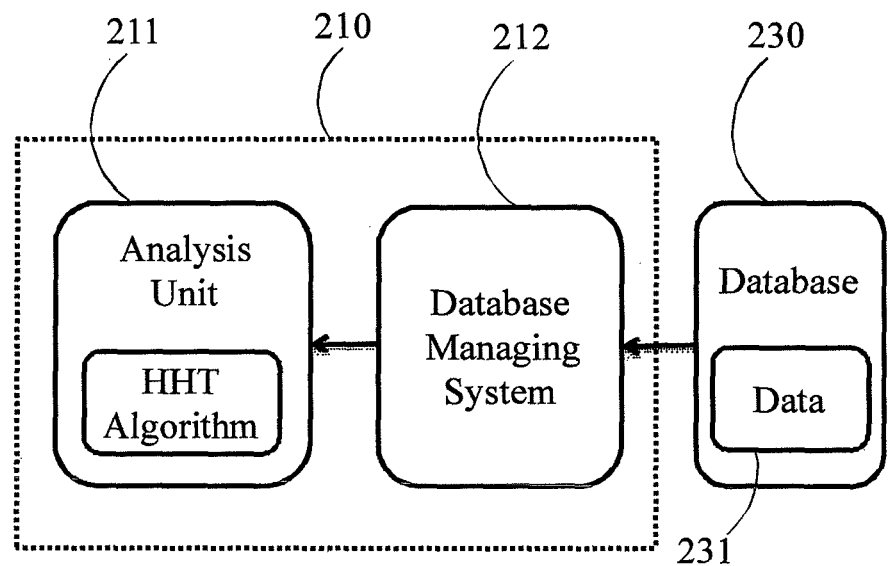
FIG. 1 shows a diagram of an analysis module in the invention.

FIG. 1 is a diagram showing an analysis module in the invention. The analysis module 210 of the invention is connected with a database 230, and the database 230 contains several data 231. The analysis module 210 comprises an analysis unit 211 and a database managing system 212.

The analysis unit 211 is developed by a development software to combine Hilbert Huang Transform (HHT) algorithm and an automatic data-loading program. The database managing system 212 is integrated in the analysis unit 211 and connected with the database 230.

In an embodiment, the development software is used to edit the codes of front segment of HHT algorithm to combine the automatic data-loading program and further to integrate and connect with the database managing system 212, but not limited herein.

In an embodiment, the development software of the invention can be MATrix LABoratory (Matlab), but not limited herein. Matlab is taken as an example, because Matlab is a kind of integrated development software, it can provide users to edit the program by himself, and can support and integrate with many kinds of software.

In an embodiment, the database managing system 212 of the invention is used to manage the data 231 of the database 230. The database managing system 212 can be MySQL, but not limited herein.

After the data 231 are transferred to the analysis unit 211 by the database managing system 212, the analysis unit 211 is used to load the data 231 by the automatic data-loading program and analyzes the data 231. The data 231 can be physiology parameter data, such as blood pressure, blood sugar, body temperature, weight and etc., but not limited herein. The data 231 contain various linear data, non-linear data, stationary data and non-stationary data, but not limited herein.

In the invention, the HHT algorithm of the analysis module 210 contains an empirical mode decomposition method, which is an adaptive analysis method, and it also can be taken as a kind of regional wave decomposition method. The HHT algorithm is based on a principle that applying reasonable and concise way to decompose any complex raw data into a number of the different simple components and a non-oscillatory residue. The component is called intrinsic mode function, and the non-oscillatory residue is called a non-oscillatory trend.

The characteristics of intrinsic mode function include reasonable instantaneous frequency definition, and can transform each component to get the information of instantaneous frequency and instantaneous amplitude over time by Hilbert transform. After mathematical calculating, a time-frequency-energy spectrum diagram is provided. It can provide good resolution, whether in the time domain or the frequency domain, and its three-dimensional distribution can reflect the inherent signal characteristics. After the Hilbert spectrum being time integral transformed, a frequency-amplitude spectrum of a two-dimensional distribution can be provided.

In other words, the database 230 of the invention can constantly store all kinds of data 231. The analysis module 210 can execute searching and reading through the database managing system 212 and the database 230. The data 231 are transferred to the analysis unit 211 by the database managing system 212, and the analysis unit 211 is used to load the data 231 by the automatic data-loading program and analyzes the data 231 to generate an analysis result.

HHT is a kind of algorithm with high efficiency, it can adjust the datum over the variation of the data. That is to say that HHT is an adaptive analysis method, it can analyze variable data over time, such as physiology parameter data. As a result, the analysis unit 211 of the invention uses HHT algorithm to analyze data. It can process data accurately and the analysis results are more referable.

Figure 2:
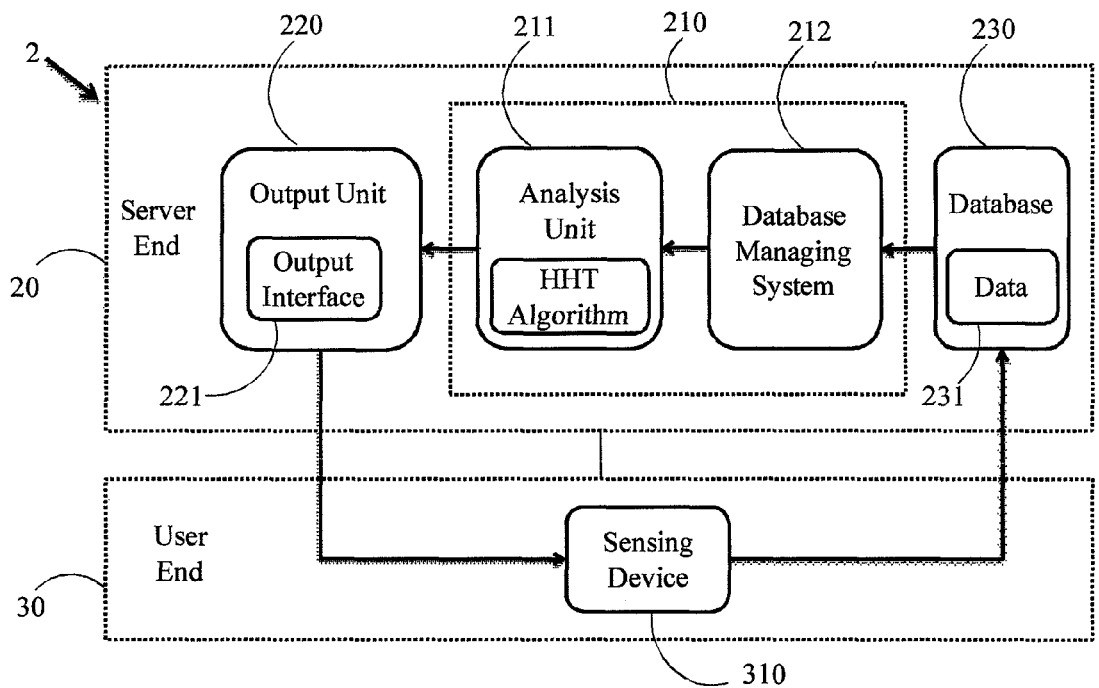
FIG. 2 shows a diagram of a cloud analysis system in the invention.

FIG. 2 is a diagram showing a cloud analysis system in the invention. The cloud analysis system 2 comprises a server end 20 and a user end 30.

The server end 20 of the invention comprises a database 230, an analysis module 210 and an output unit 220.

The database 230 comprises several data 231, and the data 231 can be physiology parameter data, such as blood pressure, blood sugar, body temperature, weight and etc., but not limited herein. The data 231 contain various linear data, non-linear data, stationary data and non-stationary data, but not limited herein.

The characteristics of the analysis module 210 of the cloud analysis system 2 in the invention are descripted above. The analysis module 210 comprises an analysis unit 211 and a database managing system 212. Wherein, the analysis unit 211 is developed by a development software to combine HHT algorithm and an automatic data-loading program. The database managing system 212 is integrated in the analysis unit 211 and connected with the database 230.

The output unit 220 of the cloud analysis system 2 comprises an output interface 221, and the output interface 221 is produced by a command line interface program or a graphical user interface (GUI) generating program. The command line interface program or the GUI generating program is Hypertext Preprocessor (PHP), but not limited herein.

The user end 30 of the cloud analysis system 2 is connected to the sever end 20. The user end 30 comprises at least a sensing device 310, and the data 231 of the database 230 are the results from the sensing device 310.

Figure 3:
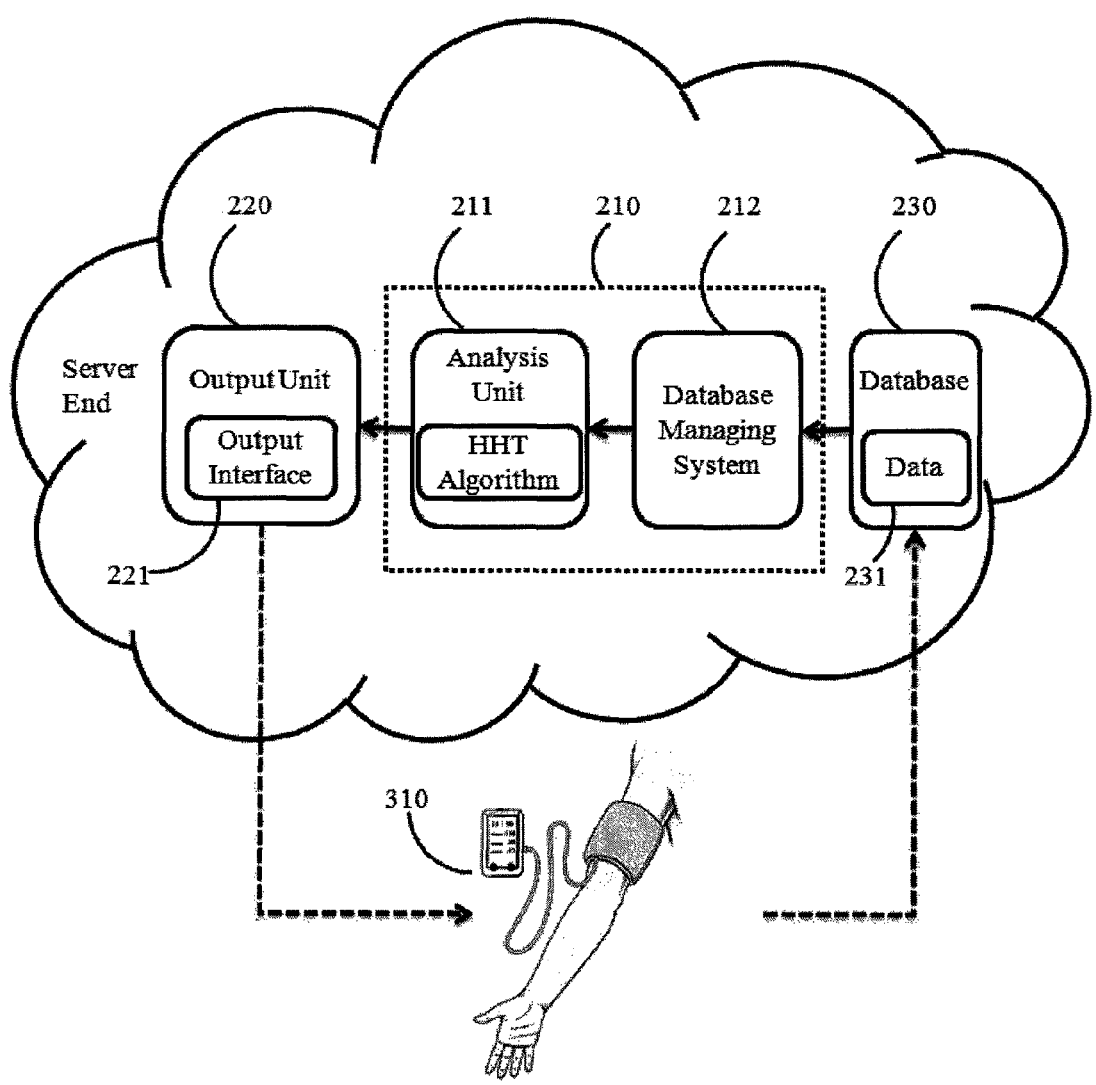
FIG. 3 shows a diagram of the sensing devices of the cloud analysis system in the invention.
Figure 4A:
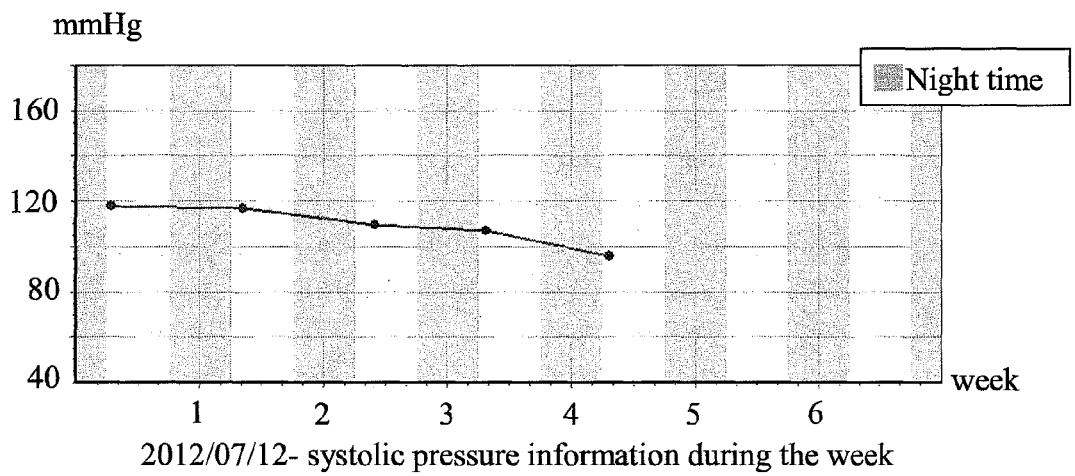
FIG. 4(a)~(c) respectively show diagrams of the systolic pressure, diastolic pressure, and heart rate information during the week, the month and the year.
Figure 4A:
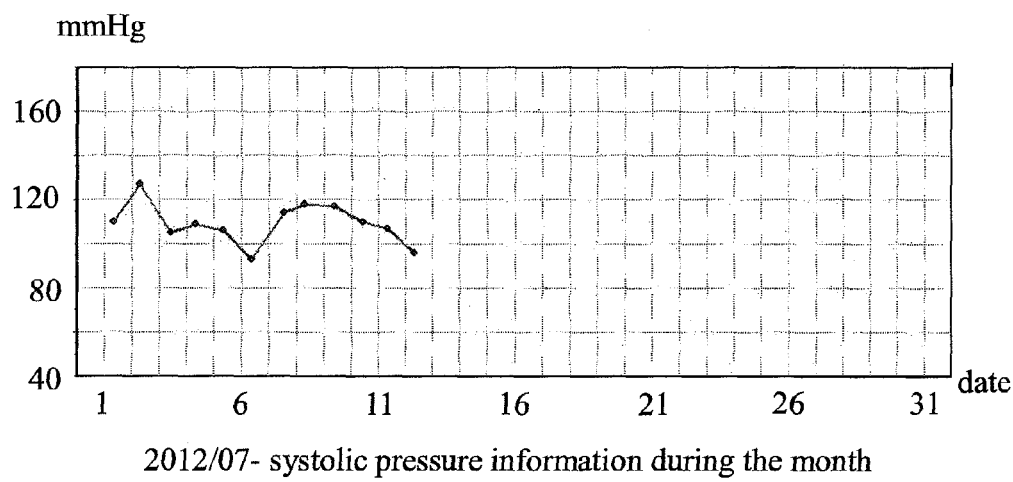
Figure 4A:
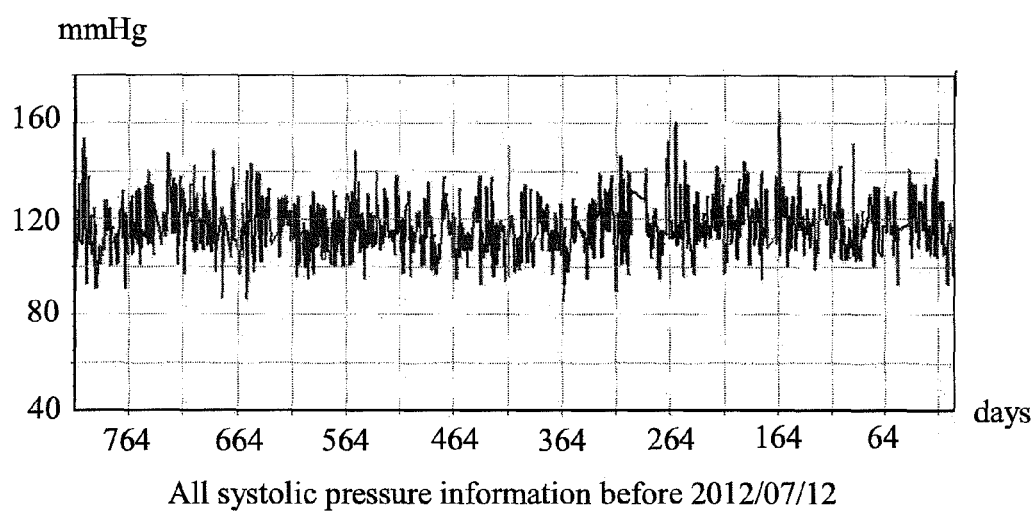
Figure 4B:
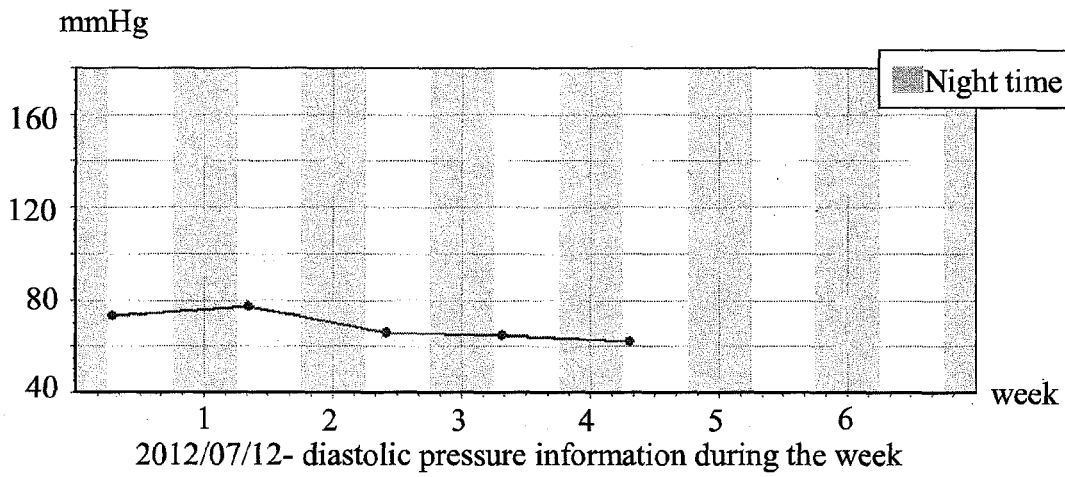
Figure 4B:
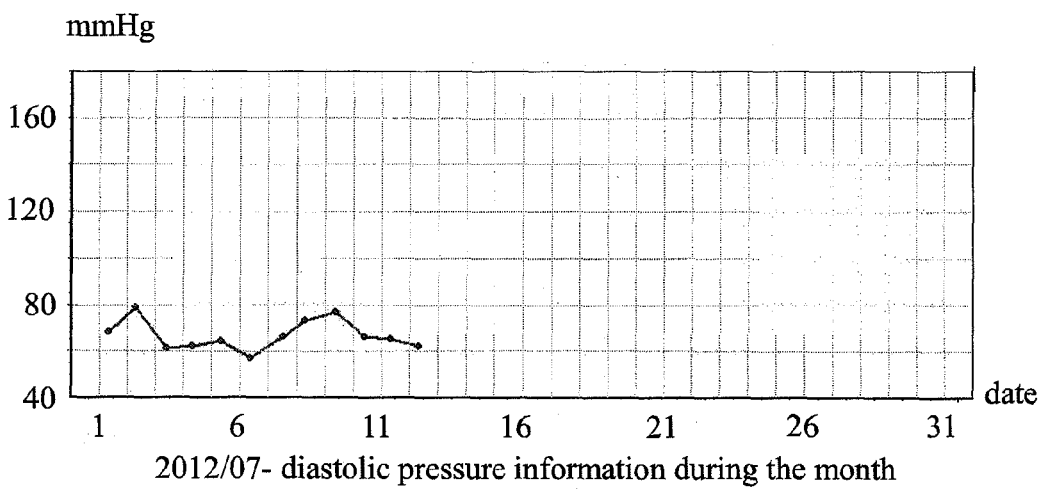
Figure 4B:
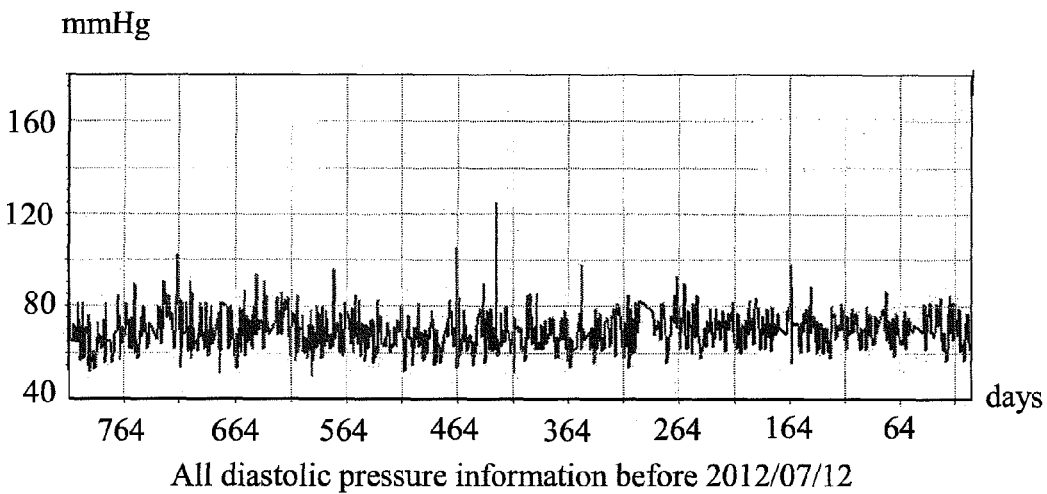
Figure 4C:
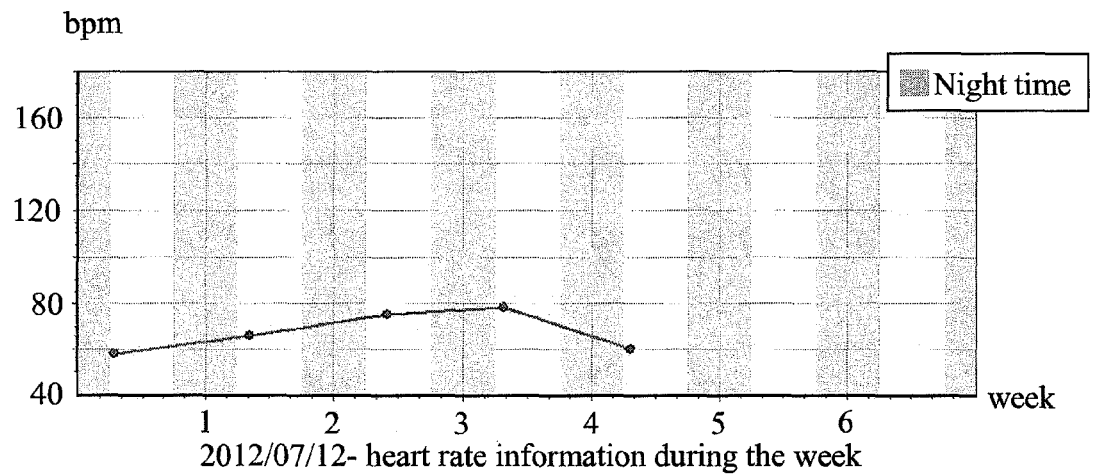
Figure 4C:
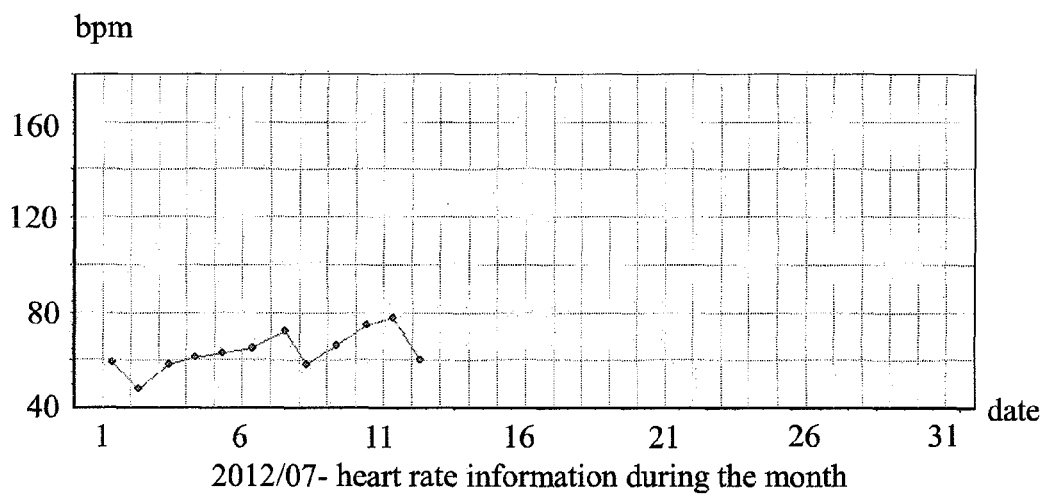
Figure 4C:
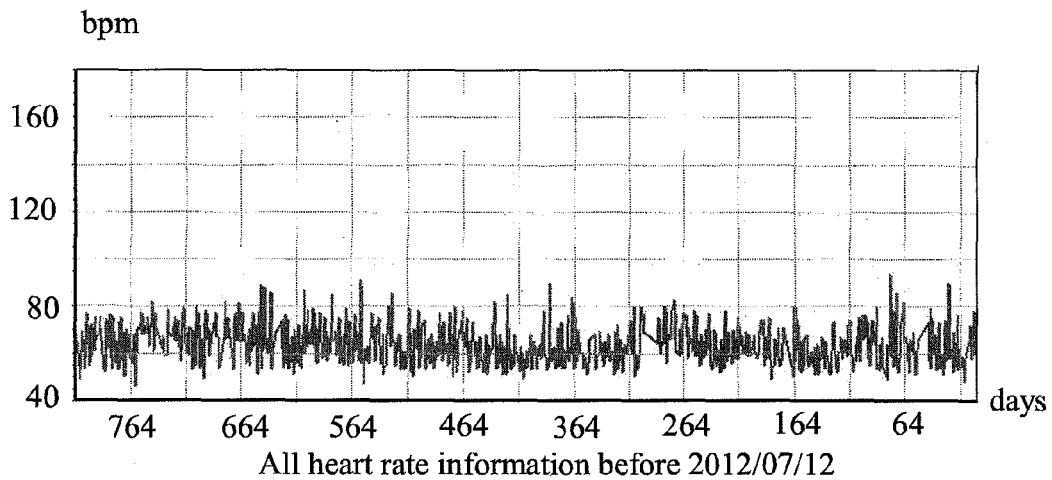

FIG. 3 is a diagram showing the sensing device of the cloud analysis system in the invention. The sensing device 310 can be any health measurement device, such as a blood pressure device, a blood sugar device, thermometers, weight device and etc., but not limited herein.

The sensing device 310 of the invention can upload physiology parameter data to the sever end 20 by wire or wireless way. The data 231 can be automatically record, stored and analyzed on network cloud to provide users fully automatic and comprehensive analysis service.

Wherein, the data 231 are transferred to the analysis unit 211 by the database managing system 212, and the analysis unit 211 is used to load the data 231 by the automatic data-loading program and analyzes the data 231.

In other words, the database 230 of the invention can constantly store all kinds of the data 231. The analysis module 210 can execute searching and reading through the database managing system 212 and the database 230. The data 231 are transferred to the analysis unit 211 by the database managing system 212, and the analysis unit 211 is used to load the data 231 by the automatic data-loading program and analyzes the data 231 to generate an analysis result. The analysis result can be displayed to the general web browser for the user's query or instantly transferred to the user by the output interface 221, but not limited herein.

As the description of above, HHT is an adaptive analysis method, it can analyze variation data over time, such as physiology parameter data. The empirical mode decomposition method can decompose any complex raw data into a number of the different intrinsic mode functions and a non-oscillatory trend and further to provide referable information. As a result, even the data 231 of the database 230 are non-linear data or non-stationary data, the analysis unit 211 still can accurately and properly process these data and make the analysis results more referable.

FIG. 4(*a*)~(*c*) are diagrams showing physiology parameter data, and blood pressure information and heart rate information are taken as examples in the invention. FIG. 4(*a*)~(*c*) respectively show the systolic pressure, diastolic pressure, and heart rate information during the week, the month and the year.

Figure 5:
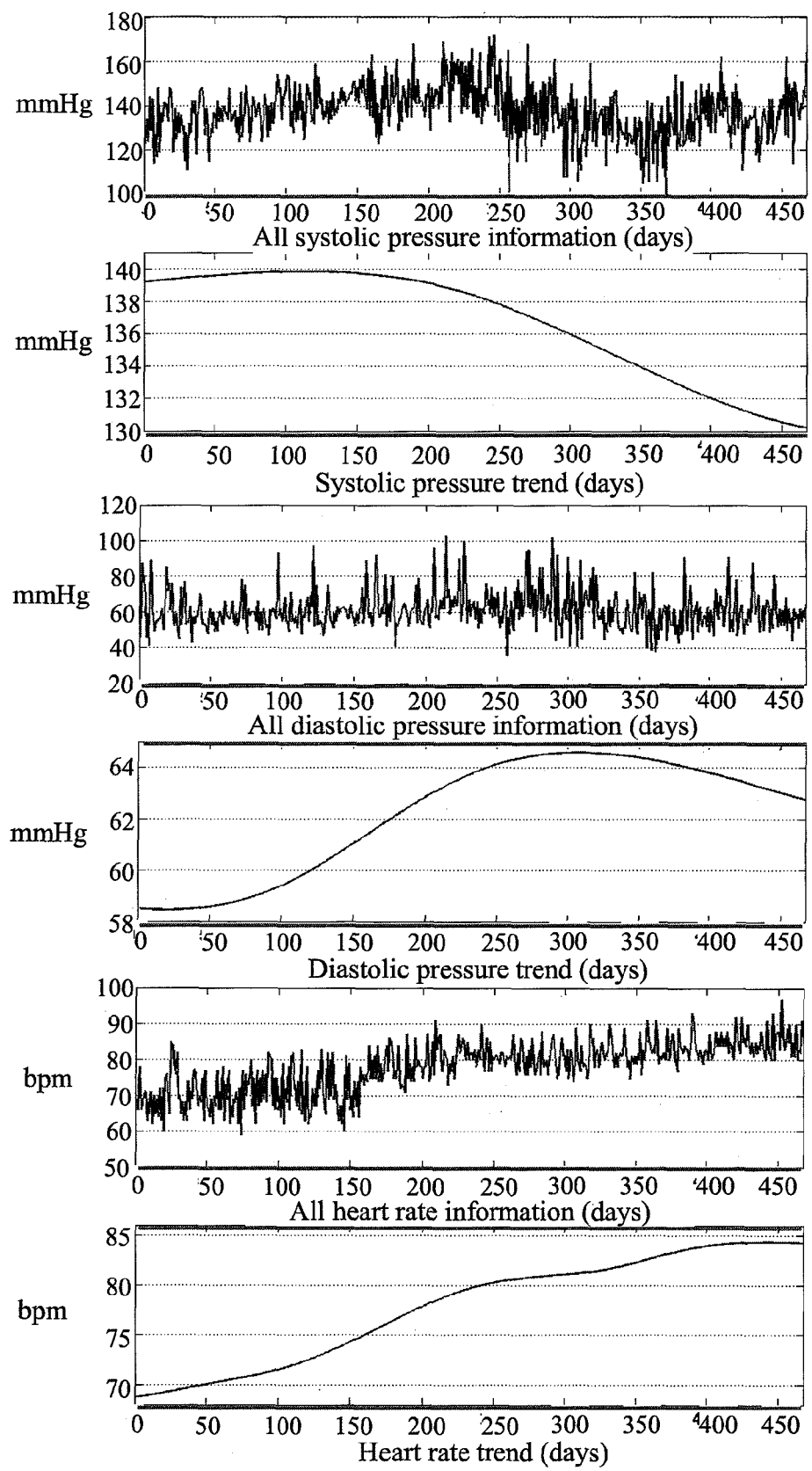
FIG. 5 shows a diagram of systolic pressure, diastolic pressure, and heart rate information and trend analysis results.

FIG. 5 is a diagram showing physiology parameter data, and blood pressure information and heart rate information are taken as examples in the invention. FIG. 5 shows the systolic pressure, diastolic pressure, and heart rate information and trend analysis results.

Figure 6:
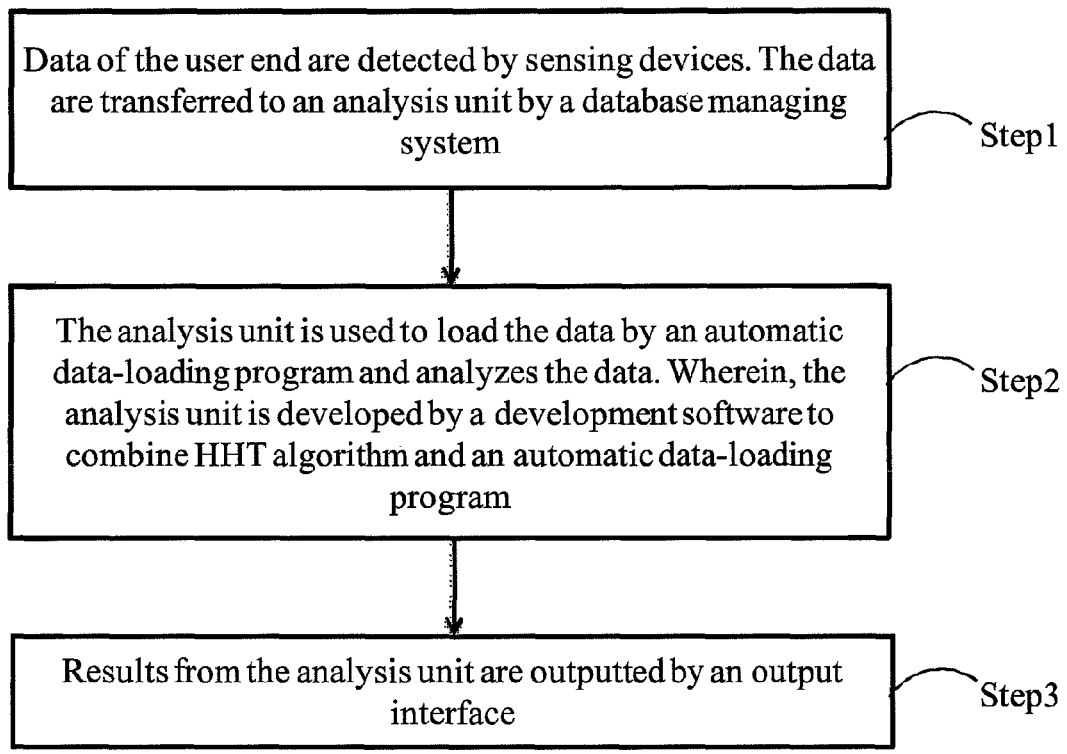
FIG. 6 shows a flowchart of the cloud analysis method in the invention.

FIG. 6 is a flowchart of the cloud analysis method in the invention. The cloud analysis method of the invention is applied to a server end, and the sever end comprises a database containing several data. The data of the database are the results from at least a sensing device. The cloud analysis method comprises the steps as follows:

Step. 1 The data are transferred to an analysis unit by a database managing system.

Step. 2 The analysis unit is used to load the data by an automatic data-loading program and analyzes the data. Wherein, the analysis unit is developed by a development software to combine HHT algorithm and an automatic data-loading program.

Step. 3 Results from the analysis unit are outputted by an output interface.

In fact, the cloud analysis system 2 of the invention is a fully automated cloud health management system. The sensing device 310, such as health measurement device, can upload physiology parameter data to the sever end 20 by wire or wireless way. The data 231 can be automatically recorded, stored and analyzed on network cloud to provide users fully automatic and comprehensive analysis service. The cloud analysis system 2 uses the empirical mode decomposition method of HHT to decompose any complex raw data into a number of different intrinsic mode functions and a non-oscillatory trend and further to provide referable information. The intrinsic mode function can be used as personal physiological parameters information of oscillation in the days, weeks, or months. The non-oscillatory trend has been ruled out transient noise or temporary fluctuations. As a result, the non-oscillatory trend can be taken as the personal physiological parameters trend. The user is allowed to easily obtain his physical condition and information through the cloud network.

Although the disclosure has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the disclosure.

What is claimed is:

1. An analysis system, connected with a database containing several data, the analysis system comprising:
   a processor that functions as an analysis unit, when a program developed by a development software is executed, to combine Hilbert Huang Transform (HHT) algorithm and an automatic data-loading program that reads the data in the database and loads the data to the analysis unit; and
   a database managing system, integrated in the analysis unit and connected with the database;
   wherein, the data are transferred to the analysis unit by the database managing system, and the analysis unit is used to load the data by the automatic data-loading program and analyzes the data,
   wherein the development software is MATrix LABoratory (Matlab), and wherein the database managing system is MySQL, and
   wherein the analysis unit analyses the data to provide an automatic and comprehensive analysis service and to provide referable information.

2. The analysis module according to claim 1, wherein the data are physiology parameter data.

3. The analysis module according to claim 2, wherein the physiology parameter data contain non-linear data and non-stationary data.

4. A cloud analysis system provided on a network, comprising:
   a server end connected to the network, comprising:
   a database, comprising data;
   a processor that functions as an analysis unit, when a program developed by a development software is executed, to combine HHT algorithm and an automatic data-loading program that reads the data in the database and loads the data to the analysis unit; and
   a database managing system, integrated in the analysis unit and connected with the database;
   wherein, the data are transferred to the analysis unit by the database managing system, and the analysis unit is used to load the data by the automatic data-loading program and analyzes the data,
   wherein the development software is MATrix LABoratory (Matlab), and wherein the database managing system is MySQL, and
   wherein the analysis unit analyzes the data to provide an automatic and comprehensive analysis service and to provide referable information.

5. The cloud analysis system according to claim 4, further comprises a user end connected to the sever end, the user end comprises at least a sensing device, and the data of the database are the results from the sensing device.

6. The cloud analysis system according to claim 4, the sever end further comprises an output unit.

7. The cloud analysis system according to claim 6, the output unit comprises an output interface.

8. The cloud analysis system according to claim 7, the output interface is produced by a command line interface program or a graphical user interface (GUI) generating program.

9. The cloud analysis system according to claim 8, the command line interface program or the GUI generating program is Hypertext Preprocessor (PHP).

10. The cloud analysis system according to claim 4, wherein the data are physiology parameter data.

11. The cloud analysis system according to claim 10, wherein the physiology parameter data contain non-linear data and non-stationary data.

12. A cloud analysis method, applied to a server end with a database containing data, the cloud analysis method comprising:
- executing a program developed by a development software to combine HHT algorithm and an automatic data-loading program on a processor so that the processor functions as an analysis unit, wherein the development software is MATrix LABoratory (Matlab);
- transferring the data to the analysis unit by a database managing system, wherein the database managing system is MySQL;
- using the analysis unit to load the data by the automatic data-loading program that reads the data in the database and loads the data to the analysis unit;
- analyzing the data; and
- outputting an analysis result,
- wherein the data is analyzed by the analysis unit to provide an automatic and comprehensive analysis service and to provide referable information.

13. The cloud analysis method according to claim 12, results from the analysis unit are outputted by an output interface.

14. The cloud analysis method according to claim 13, the output interface is produced by a command line interface program or a GUI generating program.

15. The cloud analysis method according to claim 14, the command line interface program or the GUI generating program is PHP.

16. The cloud analysis method according to claim 12, wherein the data are physiology parameter data.

17. The cloud analysis method according to claim 16, wherein the physiology parameter data contain non-linear data and non-stationary data.

* * * * *